United States Patent [19]

Cavalleri et al.

[11] 4,113,953

[45] Sep. 12, 1978

[54] 2-NITROIMIDAZOLE DERIVATIVES

[75] Inventors: Bruno Cavalleri; Giancarlo Volpe, both of Milan, Italy

[73] Assignee: Gruppo Lepetit S.p.A., Milan, Italy

[21] Appl. No.: 759,697

[22] Filed: Jan. 17, 1977

[30] Foreign Application Priority Data

Jan. 27, 1976 [GB] United Kingdom ............... 2993/76

[51] Int. Cl.² .................................. C07D 233/91
[52] U.S. Cl. ........................ 548/339; 424/273 R
[58] Field of Search ..................... 260/309; 548/339

[56] References Cited

U.S. PATENT DOCUMENTS

| 3,450,710 | 6/1969 | Verdi | 260/309 |
| 3,458,528 | 7/1969 | Gal | 260/309 |
| 3,652,579 | 3/1972 | Hoffer et al. | 260/309 |
| 3,865,823 | 2/1975 | Beaman et al. | 260/309 |
| 3,954,789 | 5/1976 | Cavalleri et al. | 260/309 |

OTHER PUBLICATIONS

Cavalleri et al. J. Med. Chemistry 1973, vol. 16, pp. 557–560.
Kollonitsch Chem. Abst. 1970, vol. 72, No. 90467w.

*Primary Examiner*—Natalie Trousof

*Attorney, Agent, or Firm*—Theodore Post; C. Kenneth Bjork; Daniel L. DeJoseph

[57] ABSTRACT

2-Nitroimidazole derivatives of the following formula:

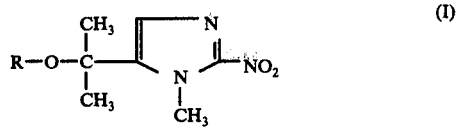

wherein R is benzoyl, phenylcarbamoyl or the group

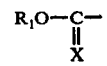

wherein $R_1$ is $C_{1-4}$ alkyl,

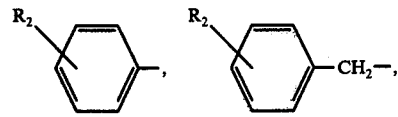

in which $R_2$ is hydrogen, halo, cyano, amino, $C_{1-2}$ alkyl, or $C_{1-3}$ alkoxy and X is oxygen or sulfur. These compounds have antimicrobial and amoebicidal utilities.

2 Claims, No Drawings

2-NITROIMIDAZOLE DERIVATIVES

SUMMARY OF THE INVENTION

The present invention concerns a new class of 2-nitroimidazole derivatives of the following formula:

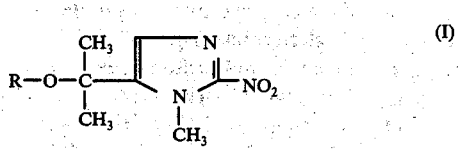

wherein R represents benzoyl, phenylcarbamoyl or the group

wherein $R_1$ represents $C_{1-4}$ straight or branched-chain alkyl,

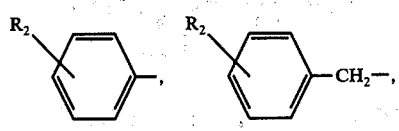

in which $R_2$ represents hydrogen, chloro, bromo, fluoro, (hereinafter "halo"), cyano, amino, $C_{1-2}$ alkyl or $C_{1-3}$ alkoxy and X is oxygen or sulfur. The inventive compounds have very interesting antimicrobial and amoebicidal utilities.

DESCRIPTION OF SOME PREFERRED EMBODIMENTS

The inventive compounds are prepared by condensing a molar amount of the compound of the formula:

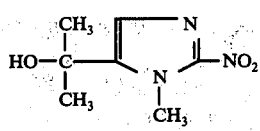

described in Belgian Pat. No. 837,595, with at least one molar equivalent of a benzoyl halide, phenylisocyanate or a compound of the formula

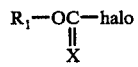

wherein $R_1$ and X are defined as above.

The reaction is preferably carried out in an organic solvent such as, for instance, benzene, toluene, dioxane, lower halogenated hydrocarbons or tertiary organic nitrogen-containing bases such as, for instance, pyridine, quinoline, isoquinoline and their lower alkyl homologs. The tertiary organic nitrogen-containing bases are most conveniently employed when a benzoyl halide or a compound of the formula

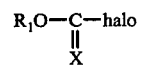

is employed as the co-reactant since they neutralize the acidity which forms during the reaction course and contemporaneously act as reaction solvents. The reaction temperature is preferably kept between about 0° C. and about room temperature and the reaction is completed within about 5 hours. The final compounds of formula (I) are then recovered from the reaction medium according to usual procedures.

The inventive compounds have very interesting antimicrobial and amoebicidal utilities which are ascertained through the usual and well known in vitro tests. Moreover, they display an outstanding in vivo activity against *Trichomonas vaginalis*, a protozoan which is responsible for itching and other painful and troublesome diseases of the vaginal tract. Their in vivo activity, expressed as an $ED_{50}$ value, is better than that of other known 2-nitroimidazole derivatives, and their activity is, moreover, coupled with a very low toxicity, expressed as an $LD_{50}$ value. These properties indicate that the compounds of the invention are very promising anti-Trichomonas agents both from the effectiveness and the safety standpoint, owing to their low $LD_{50}$ values and their high therapeutic indexes (T.I.). Since a therapeutic index is expressed by the following ratio:

$$LD_{50}/ED_{50},$$

it is clear that the higher the T.I., the safer a drug is.

In the following Table, results representative of the inventive compounds are reported. They show that the compound of Example 1 possesses a better $ED_{50}$ and a better T.I. than metronidazole[1-(2-hydroxyethyl)-2-methyl-5-nitroimidazole], which is the most widely employed drug in the treatment of infections due to *Trichomonas vaginalis*.

TABLE

| Compound of Example | $ED_{50}$, mg/kg per os, mice | $LD_{50}$, mg/kg per os, mice | T.I. ($LD_{50}/ED_{50}$) |
|---|---|---|---|
| 1 | 1.65 | 3250 | 1969 |
| metronidazole | 5.77 | 3800 | 658 |

The compounds of the invention may be administered by various routes, for example, orally, subcutaneously or topically. For oral administration, the compounds are compounded in such forms as tablets, dispersible powders, capsules, syrups and solutions. Tablets may contain the active compounds admixed with conventional pharmaceutically-acceptable excipients, e.g., inert diluents such as calcium carbonate, lactose and talc; granulating and disintegrating agents, such as, for instance, starch, alginic acid and sodium carboxymethylcellulose; binding agents, e.g., starch, gelatin, gum arabic and polyvinylpyrrolidone; and lubricating agents, e.g., magnesium stearate, stearic acid and talc.

Syrups and solutions are formulated in usual ways. Together with the active compounds, they may contain suspending agents, such as, for instance, methylcellulose, hydroxyethylcellulose, tragacanth and sodium alginate; wetting agents, e.g., lecithin, polyoxyethylene stearates and polyoxyethylene sorbitan monooleate; and the common preservatives, sweetening and buffering agents. A capsule or a tablet may contain the active compounds alone or admixed with an inert solid diluent, such as, for instance, calcium carbonate, calcium phosphate and kaolin. For topical administration, the active compounds of formula (I) are compounded into ointments or vaginal inserts.

The following additional description and examples further describe the invention and the manner and process of making and using it to enable the art skilled to make and use the same and set forth the best mode contemplated by the inventors of carrying out the invention.

EXAMPLE 1

α, α,1-Trimethyl-2-nitroimidazole-5-methanol phenylcarbonate

To a cold pyridine solution of 7.8 g (0.042 mole) of 5-[(1-hydroxy-1-methyl)ethyl]-1-methyl-2-nitroimidazole, 5.3 ml (0.042 mole) of phenyl chloroformate are added dropwise. The resulting mixture is stirred for four hours at room temperature and then is left standing overnight. On pouring onto crushed ice with stirring, a product separates which is filtered and crystallized from ethanol. Yield 3.8 g of the title compound. M.p. 113°–15° C.

EXAMPLE 2

α, α, 1-Trimethyl-2-nitroimidazole-5-methanol phenylcarbamate

Two and six-tenths ml (0.024 mole) of phenyl isocyanate are added dropwise to a solution of 3 g (0.0176 mole) of 5-[(1-hydroxy-1-methyl)ethyl]-1-methyl-2-nitroimidazole in 25 ml of anhydrous pyridine at room temperature with stirring. The resulting solution is heated at about 80° C. for 5 hours, then 2 ml (0.0168 mole) of phenylisocyanate are added and heating is carried on for another hour. After cooling to room temperature, 50 ml ligroin is added to the reaction mixture and an oily product separates which, after elimination of the liquors by decantation, is taken up with diethyl ether. A solid product is obtained which is recrystallized from benzene. Yield of title compound 1.18 g. M.p. 155°–158° C.

EXAMPLE 3

α, α, 1-Trimethyl-2-nitroimidazole-5-methanol benzoate

Eight-tenths ml (0.00736 mole) of benzoyl chloride is added dropwise to a solution of 3 g (0.0176 mole) of 5-[(1-hydroxy-1-methyl)ethyl]-1-methyl-2-nitroimidazole in 10 ml of anhydrous pyridine at room temperature with stirring. After adding 6 ml of anhydrous pyridine and 1.6 (0.0145 mole) of benzoyl chloride dropwise, the resulting solution is stirred for 5 hours and 50 ml diethyl ether is then added thereto. An oily product separates which, after elimination of the liquors by decantation, is washed twice with two 20 ml portions of water, dried over sodium sulfate and crystallized from diethyl ether-liquid petrolatum. The obtained solid is further purified by column chromatography by eluting first with chloroform and then with chloroform:methanol=1:1. The fractions eluted with the chloroform and methanol in the above ratio are collected, the solvent is evaporated off in vacuo and the obtained residue is recrystallized from diisopropyl ether. Yield of title compound 0.280 g. M.p. 125°–128° C.

We claim:
1. The compound of the formula

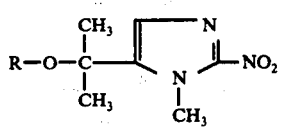

wherein R is benzoyl, phenylcarbamoyl or the group

wherein $R_1$ is straight or branched-chain $C_{1-4}$ alkyl,

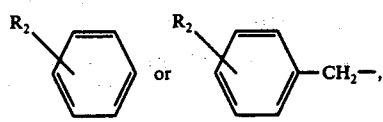

in which $R_2$ is hydrogen, halo, cyano, amino, $C_{1-2}$ alkyl or $C_{1-3}$ alkoxy and X is oxygen or sulfur.

2. A compound as defined in claim 1 which is the α,α,1-trimethyl-2-nitroimidazole-5-methanol phenylcarbonate.